United States Patent
Sabuda

Patent Number: 6,132,357
Date of Patent: Oct. 17, 2000

[54] METHOD OF ENERGIZING AND USING AN OBJECT FOR STIMULATING BIOLOGICAL PROCESSES

[76] Inventor: Thomas J. Sabuda, 71 N. Edgewood Dr., Springville, N.Y. 14141

[21] Appl. No.: 09/264,525

[22] Filed: Mar. 8, 1999

Related U.S. Application Data

[63] Continuation-in-part of application No. 09/114,861, Jul. 13, 1998.

[51] Int. Cl.[7] .............................. A61N 5/00; A61N 1/00; A61B 17/52; A61B 17/38; A61F 2/00
[52] U.S. Cl. ................................... 600/1; 600/9; 606/33; 607/2; 607/100
[58] Field of Search ................................... 600/1, 2, 3, 9, 600/12, 13, 14; 607/1, 2, 100; 606/33, 32

[56] References Cited

U.S. PATENT DOCUMENTS

| | | |
|---|---|---|
| 5,086,770 | 2/1992 | Prangley . |
| 5,562,597 | 10/1996 | Van Dick . |
| 5,792,184 | 8/1998 | Zhou et al. .................................. 607/1 |
| 5,807,233 | 9/1998 | Sakuma et al. . |
| 5,814,078 | 9/1998 | Zhou et al. . |

*Primary Examiner*—Cary O'Connor
*Assistant Examiner*—Navin Natnithithadha
*Attorney, Agent, or Firm*—Hodgson, Russ, Andrews, Woods & Goodyear, LLP

[57] ABSTRACT

A substantially ungrounded crystal that has at least one external line angle emits a low level energy field about itself when an electromagnetic radiation is incident to its surface. An unenergized object may be placed in the field and energized such that the object may be used to stimulate biological processes when placed in proximity to the tissues to be stimulated.

20 Claims, 2 Drawing Sheets

METHOD OF ENERGIZING AND USING AN OBJECT FOR STIMULATING BIOLOGICAL PROCESSES

CROSS REFERENCE TO RELATED APPLICATION

The present application is a continuation-in-part of patent application Ser. No. 09/114,861, filed Jul. 13, 1998, and entitled Method and Device for Stimulating Biological Processes, which is hereby incorporated by reference.

FIELD OF INVENTION

This patent relates to methods of energizing and using objects for stimulating biological processes and specifically to a method of utilizing the radiations emitted about a selected crystal to energize an unenergized object which can be placed in proximity to a biological system for the purpose of stimulating biological processes within the biological system.

BACKGROUND OF THE INVENTION

Living organisms are known to emit electromagnetic radiations (em radiations) and to respond to em radiations. Low level energies that operate in biological systems that generate the em radiations are classified as bio-energies. The low level em radiations generated by living systems also can influence other living systems within their respective spheres of influence. Also, there are other low level em radiations present in the natural environment that influence the bio-energies of living systems. These natural environmental radiations include celestial radiations originating in the earth's atmosphere and beyond the earth's atmosphere and all terrestrial radiations. That these radiations influence living systems cannot be denied even though their manner of influencing often cannot be explained with any degree of certainty. Life developed under the influences of low level environmental radiations. So, from an evolutionary standpoint, it is reasonable to conclude that all em processes present in the environment played a formative role in the development of all living organisms even though their significance may be overlooked.

The use of em radiations emitted from the human body was documented in ancient China. The Chinese called this externally radiated bio-energy "Qi Gong energy." Omura has demonstrated the existence of the Qi Gong energy and that the human can emit this Qi Gong bio-energy from the hands, fingers, feet, and eyes (see Omura, Y.; Lin, T. L.; Debrecini, L.; Losco, M.; Freed, S.; Muteki, T.; and Lin, C. H., "Unique changes found on the Qi Gong (Chi Gong) Master's and patient's body during Qi Gong treatment: Their relationships to certain meridians and acupuncture points and the re-creation of therapeutic Qi Gong states by children and adults," *Acupuncture & Electro-Therapeutics Research,* 1989; 14: 61–89). Qi Gong masters can emit the Qi Gong energy for therapeutic purposes when they create certain specified internal conditions within themselves. Omura, after extensively studying the properties of the emitted Qi Gong energy discovered that many inanimate objects can "store" (as termed by Omura) the emitted Qi Gong energy as a result of the intentional directing of the Qi Gong energy into the inanimate objects by the Qi Gong master. Omura also discovered that the inanimate objects storing the Qi Gong energy radiate the Qi Gong energy spontaneously and continuously as long as the objects are not exposed to certain electromagnetic fields which can erase the stored energy. Omura also discovered that the so radiating inanimate object has therapeutic utility as a device to apply its radiating energy which has a therapeutic efficacy comparable to the Qi Gong energy emitted directly from a Qi Gong master (see Omura, Y., "Storing of Qi Gong energy in various materials and drugs (Qi Gongnization): its clinical application for treatment of pain, circulatory disturbance, bacterial or viral infections, heavy metal deposits and related intractable medical problems by selectively enhancing circulation and drug uptake," *Acupuncture & Electro-Therapeutics Research,* 1990; 15: 137–157). The author of the present invention suggests that the "stored" Qi Gong energy and the inanimate object storing it may best be understood by comparing them to a magnetic field and the magnet from which the magnetic field emanates. The object radiating the stored Qi Gong energy exhibits two opposing polarities just as a magnet has opposing North and South poles. One polarity is stimulative for biological processes and the other polarity is inhibitive for biological processes. That aspect of the object which emits the "stored" stimulative Qi Gong energy is positioned so as to face the area of the organism which is to receive the stimulative Qi Gong energy.

Prior Art contains several devices for generating weak stimulative energy. U.S. Pat. No. 5,792,184 to Zhou et al. (1998) and U.S. Pat. No. 5,814,078 to Zhou et al. (1998) disclose a method and apparatus for generating a biofrequency spectrum by stimulating chemical elements and chemical compounds with thermal energy or magnetic energy. The apparatus is made by incorporating exact proportions of chosen chemical elements and chosen chemical compounds within a composition. The method of using the apparatus requires stimulation of the composition by thermal energy generated within the composition by electrical resistance heat sources or an external heat source, such as body heat. U.S. Pat. No. 5,562,597 to Van Dick (1996) discloses an apparatus fabricated by placing an electrical conductor, which is connected to an electrical pulse generator, adjacent to a quartz crystal. When the pulse generator is activated, an electromagnetic field (emf) generated about the conductor stimulates the quartz crystal to emit a weak emf about itself. A subject is positioned within the so generated emfs for biostimulation. Magnetic field energy is also a source of stimulative energy. U.S. Pat. No. 5,807,233 to Sakuma et al. (1998) discloses a device which is worn on the body and which is made by including permanent magnets in the device. U.S. Pat. No. 5,086,770 to Prangley (1992) discloses a therapeutic apparatus having a light/heat source which is incident to a plurality of jewels mounted in a disc of silver or gilded copper. A therapeutic radiation emerges from the jewels.

A drawback of some prior art devices is the lack of portability during their use. Another drawback of some devices is that the device which ultimately effects biostimulation can be somewhat obtrusive to wear and, outside of permanent magnets, requires an energy input to generate a radiation which can be directed toward the living system to be stimulated. An improvement would be a device that spontaneously emits a low level energy capable of stimulating biological processes without using permanent magnets and has total portability during use.

SUMMARY OF THE INVENTION

A substantially ungrounded crystal that has at least one external line angle will emit a low level energy field about itself when an electromagnetic radiation is incident to its surface. The author of the present invention gives the low level energy field so emitted about the crystal the designation crystal photon field ("cpf"). While radiation within the radiation spectrum that includes x-ray, ultraviolet, visible light, and infrared radiations is incident to the surface of the substantially ungrounded crystal, the cpf emitted about the crystal has the potential to stimulate biological processes. The author of the present invention discovered that the cpf energizes certain materials in a manner that results in the aforementioned materials emitting an autonomous energy that also has the potential to stimulate biological processes. The author of the present invention additionally discovered that, in order for the crystal to emit a cpf that energizes certain materials, certain conditions must exist. A first condition is that the crystal(s) must be substantially ungrounded. A second condition is that the crystal(s) must have at least one external line angle. A third condition is that the crystal(s) has no contact with metal and no metal is in proximity to the crystal. A fourth condition is that, in those radiation generators powered by alternating current, the housing of the radiation generator must have an electrical ground. When the aforementioned conditions exist, the cpf emitted from the crystal, while a radiation wavelength(s) is incident to the crystal, will energize certain materials. The materials that are energizable by the cpf have compositions which include polar molecules, polymers with asymmetry and non-crystalline anisotropic textures containing some degree of asymmetric molecules and/or crystalline subunits. The author of the present invention discovered that so energized materials spontaneously emit a radiation that stimulates biological processes. However, there remain many unexplained aspects to the process of energizing materials with an energy that is capable of stimulating biological processes.

A material that is energized by a cpf usually has a polarity. The most convenient material form to use is a flat sheet. The energized sheet is placed in proximity to the tissues to be stimulated and the side of the sheet emitting the stimulative energy faces the tissue. Usually, the side of the sheet that faces the crystal(s) during the energizing process emits the stimulative energy.

In accordance with the present invention, a method of energizing an unenergized object for stimulating biological processes having considerable advantage over prior art is provided. In an exemplary embodiment of the method of the present invention, a low pressure mercury vapor lamp ("lpmv") lamp is positioned in proximity to a pyramidally shaped rose quartz crystal. An ultraviolet ("uv") radiation, which consists predominantly of 253.7 nanometer ("nm") wavelength radiation, is present between the lpmv lamp and the rose quartz crystal when the lpmv lamp is energized. While the uv radiation is incident to the surface of the rose quartz crystal, a concomitant low level radiation, which is an emission from the crystal, is present about the crystal. The author of the present invention has given the low level radiation emitted from the crystal the designation cpf. While the low level cpf is present about the crystal, a suitable material, such as a paper sheet, is placed in proximity to the rose quartz crystal. After cessation of the uv radiation incident to surface of the crystal, that aspect of the now energized paper sheet emitting the stimulative radiation is placed in proximity to a biological process. Most commonly the biological process is within a tissue of a living organism but in vitro biological processes can also be stimulated.

OBJECTS AND ADVANTAGES

Accordingly, several objects and advantages of the method of the present invention are:

(a) to provide a novel method of energizing an unenergized object which spontaneously emits a low level energy that stimulates biological processes;

(b) to provide a method for energizing an unenergized object which is safe and easy to use;

(c) to provide a method for energizing an unenergized object which can be comprised of readily available materials;

(d) to provide a method of energizing an unenergized object which can be stored almost indefinitely;

(e) to provide a method of energizing an unenergized object which requires no additional energy input into the energized object after the initial energizing process in order for the energized object to be operative;

(f) to provide a method of energizing an unenergized object which utilizes the energy imprint of a crystal photon field.

The above and yet other objects and advantages of the method of the present invention will become apparent from the hereinafter set forth Brief Description of the Drawings, Utilization Procedure and claims.

BRIEF DESCRIPTION OF THE DRAWINGS

With reference to FIG. 1, there is shown a crystal photon field ("cpf") generator 10 and a cpf 11 disposed about the cpf generator 10. An unenergized object 12 suitable for energizing in the cpf 11 has a position in proximity to the cpf generator 10 and within the cpf 11.

FIG. 2 shows the relationship of the low pressure mercury vapor ("lpmv") lamp 13 to a pyramidally shaped rose quartz crystal 15 and the ultraviolet (uv) radiation 14 located between the lpmv lamp 13 and the rose quartz crystal 14 along with the position of a paper sheet object 16 positioned in proximity to the rose quartz crystal 15. The rose quartz crystal 15 is electrically insulated such that it is substantially ungrounded. The crystal 15 has multiple faces 23 that intersect with one another along external line angles 26.

FIG. 3 shows an x-ray radiation generator 17 positioned in proximity to a calcite crystal 19 located on top of a leather sheet object 20 and an x-ray radiation 18 located between the x-ray radiation generator 17 and the calcite crystal 19.

UTILIZATION PROCEDURE

Figure 1:
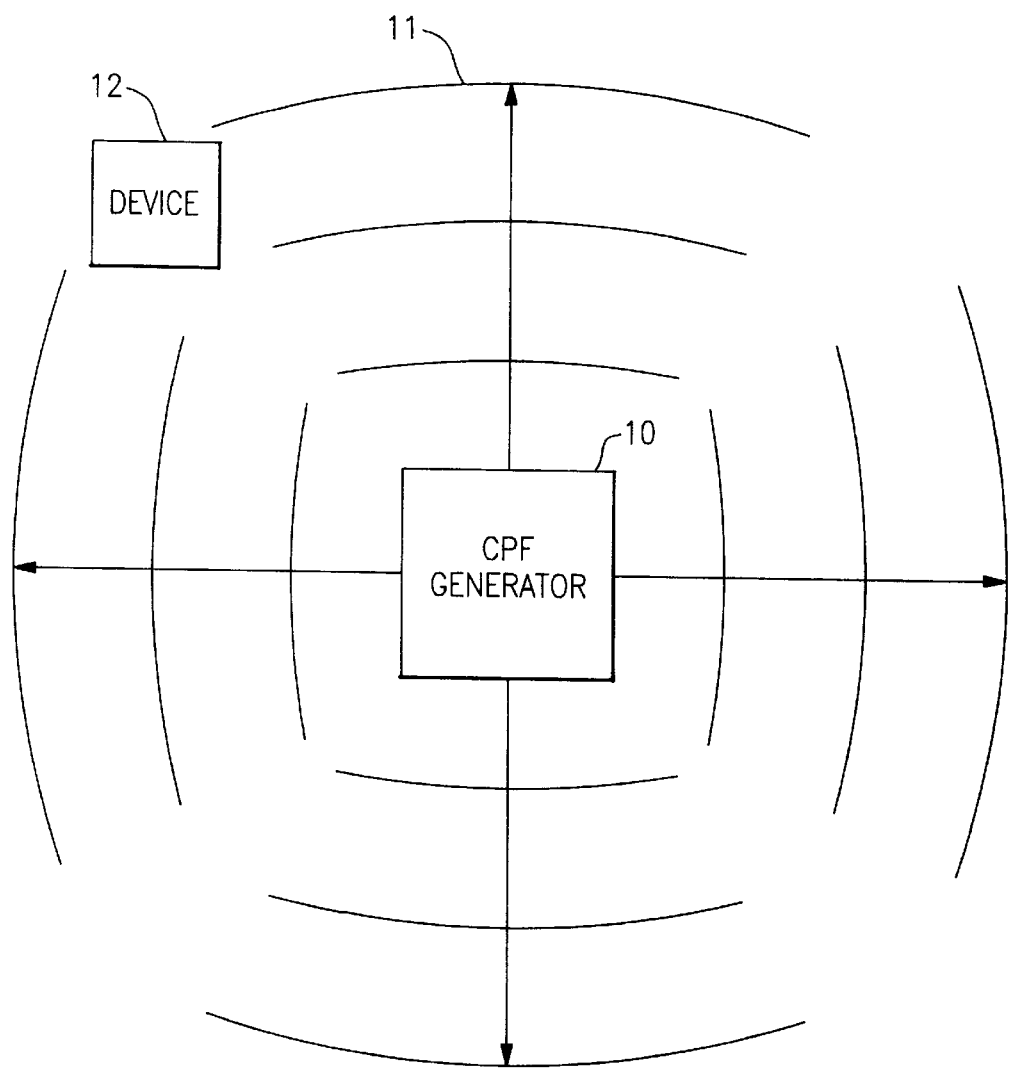
FIG. 1 is a schematic diagram of the present invention.
Figure 3:
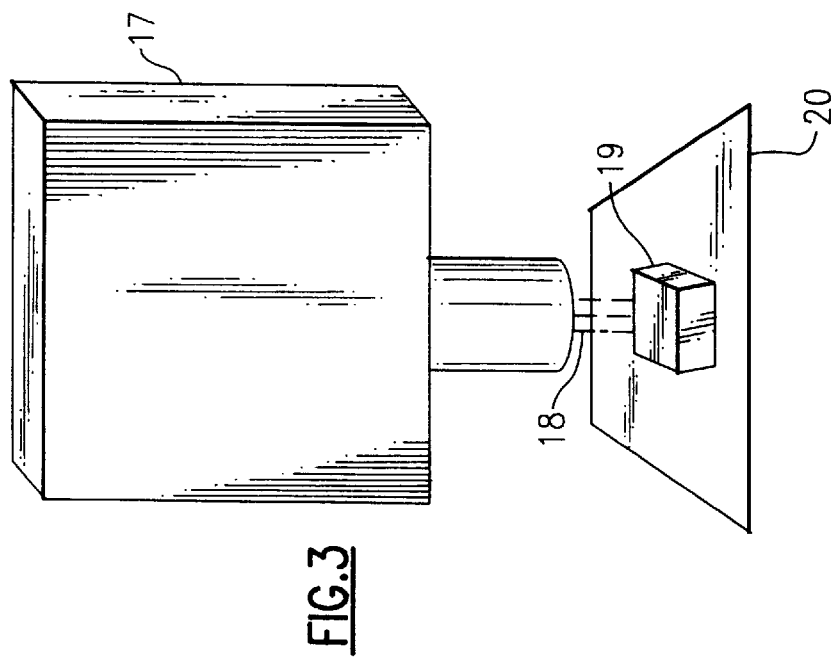
FIG. 3 is a perspective view of an alternate embodiment of the present invention.
Figure 2:
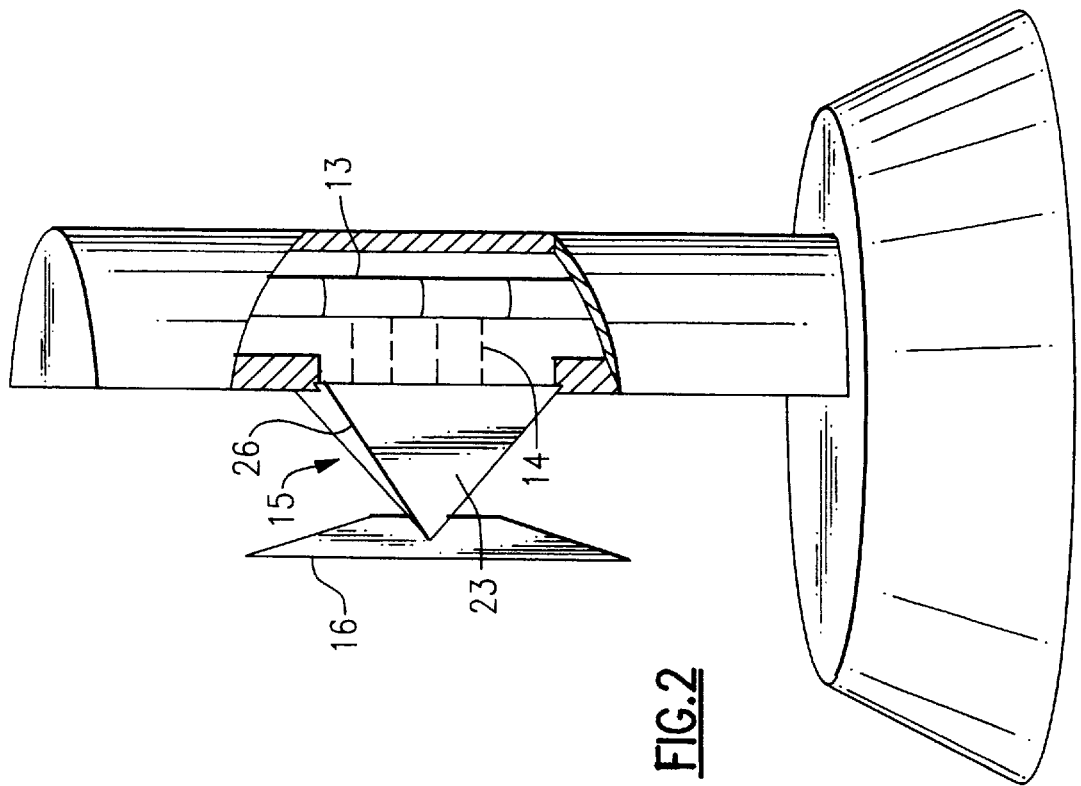
FIG. 2 is a side elevational view of an embodiment of an apparatus used in the method of the present invention.

The preferred embodiment of the present invention utilizes a lpmv lamp 13 to emit an ultraviolet radiation 14 which is directed so as to be incident to the base of a pyramidally shaped rose quartz crystal 15. The ultraviolet radiation 14 is contiguous with the rose quartz crystal 15 and has an intensity consisting of 50 micro watts per square centimeter for the radiation wavelengths less than 300 nm and 100 micro watts per square centimeter for the radiation wavelengths greater than 300 nm. Prior to energizing the lpmv lamp 13, an unenergized paper sheet object 16 is positioned in proximity to the apex of the rose quartz crystal 15. The ultraviolet radiation 14 is delivered to the surface of the rose quartz crystal 15 for a time period consisting of at least 30 seconds. After cessation of the ultraviolet radiation 14, the paper sheet object 16 is placed in proximity to the area of the living system to be stimulated. That aspect of the energized paper sheet object 16 that is directed toward the living system is the aspect of the energized paper sheet that faced the rose quartz crystal 15 while the ultraviolet radiation 14 incident to the rose quartz crystal 15. The energized paper sheet object 16 is placed in contact with or in proximity to the living system for a time duration appropriate for the circumstances of the area of the living system to be stimulated. Alleviation of pain may manifest within a time duration ranging from 10 seconds to one hour. An increase in the blood and lymph circulation within the area of the living system that receives stimulation from the energized paper object 16 can also begin to manifest within the initial 15 minute time duration.

Another method for making a device for stimulating biological processes utilizes an x-ray radiation generator 17. The procedure of another method for making a device for stimulating biological processes comprises generating an x-ray radiation 18 at 80 KVP and 15 MA for a time period consisting of 20 seconds. The x-ray radiation 18 is incident to a calcite crystal 19 which is located on a leather sheet object 20. The method of using the leather sheet object 20 is to place the aspect of the energized leather sheet object 20 that faced the calcite crystal 19 during the energizing process toward the living system for biostimulation.

While the description of the preferred embodiments of the method of the present invention contains many specificities, these should not be construed as limits on the scope of the invention, but rather as an exemplification of the preferred embodiments thereof. Many other variations are possible and that are within the scope and spirit of the invention. Other radiation sources for generating the radiation(s) incident to the crystal(s) may be selected from the radiation source group consisting of, but not limited to, other x-ray radiation generators, visible light sources, long wavelength ultraviolet radiation generators and infrared radiation generators. Multiple radiation generators and multiple crystals may be utilized simultaneously. Other crystals may be selected from the crystal group consisting of, but not limited to, other silicates, phosphates, other carbonates, diamonds, synthetic crystals, oxides, organic crystals, crystals in solution and crystal aggregates such as granite. Also, the crystal may assume a shape selected from, but not limited to, the shape group consisting of cube, obelisk, hexahedron, disk, and any rough crystalline form. The object that is energized according to the method of the present invention may consist of other materials selected from the material group consisting of, but not limited to, plastics, polyesters, synthetic textiles, cellulose and materials at least partially made from cellulose, cotton and cotton containing materials, silk, linen, ramie, rayon, leather, materials at least partially made from collagen, and other materials made from molecules with noncentrosymmetric structure. From the foregoing, it will be obvious to those skilled in the art that various modifications in the above described method and device can be made without departing from the spirit and essential characteristics thereof. Present embodiments, therefore, are to be considered in all respects as illustrative and not restrictive. The scope of the invention is indicated by the appended claims rather than by the foregoing description and all changes which come within the meaning and ranges of equivalence of the claims are therefore intended to be embraced therein.

What is claimed:

1. A method for energizing at least one unenergized object for stimulating biological processes comprising:

providing at least one radiation source capable of emitting radiation having a wavelength between $10^{-3}$ nm and $10^3$ nm;

directing the radiation to be incident to at least one crystal;

positioning at least one unenergized object in proximity to the at least one crystal while the radiation is incident to the at least one crystal, whereby the at least one unenergized object becomes energized and is usable for stimulating biological processes.

2. The method for energizing a unenergized object for stimulating biological processes according to claim 1, wherein said crystal comprises at least one element selected from the element group consisting of aluminum, antimony, arsenic, barium, beryllium, boron, bromine, cadmium, calcium, carbon, cesium, chlorine, chromium, cobalt, copper, fluorine, gold, hydrogen, iodine, iron, lithium, lead, magnesium, manganese, mercury, molybdenum, nickel, nitrogen, oxygen, palladium, phosphorus, platinum, potassium, radium, selenium, silicon, silver, sodium, strontium, sulfur, tellurium, tin, titanium, tungsten, uranium, vanadium, zinc, and zirconium.

3. The method for energizing an unenergized object for stimulating biological processes according to claim 1, wherein the crystal comprises at least one ion selected from the group consisting of aluminum, antimony, arsenate, borate, cadmium, calcium, carbide, carbonate, cesium, chromate, chromium, cobalt, copper, halide, hydride, iron, lithium, magnesium, manganese, mercury, molybdate, nickel, nitrate, nitrite, oxide, palladium, phosphate, platinum, potassium, selenium, silicate, silver, sodium, sulfate, sulfide, sulfite, tin, tungstate, vanadate, and zinc.

4. The method for energizing an unenergized object for stimulating biological processes according to claim 1 wherein the crystal is comprised of a mineral selected from the mineral group consisting of albite, amethyst, anhydrite, apatite, aragonite, azurite, barite, beryl, biotite, borax, brochantite, bromellite, calcite, carnotite, celestite, chalcocite, chromite, corundum, cristobalite, crocoite, cryolite, diamond, diaspore, diopside, dolomite, fluorite, garnet, halite, hornblende, ice, lazulite, leucite, malachite, mercury, microcline, muscovite, nepheline, niter, opal, orthoclase, periclase, pyrite, quartz(es), realgar, rutile, scheelite, silver, sodalite, sulfur, sylvite, tellurium, titanite, tourmaline, tremolite, turquoise, willemite, wolframite, wulfemite, and zircon.

5. The method for energizing an unenergized object for stimulating biological processes according to claim 1 wherein the crystal is a synthetic crystal.

6. The method for energizing an unenergized object according to claim 1 wherein the crystal is a crystal consisting of an organic molecule.

7. The method for energizing an unenergized object for stimulating biological processes according to claim 1 wherein the crystal is substantially ungrounded.

8. The method for energizing an unenergized object for stimulating biological processes according to claim 7 wherein the crystal has at least one external line angle.

9. The method for energizing an unenergized object for stimulating biological processes according to claim 8 wherein the crystal is contiguous to a nonmetal member.

10. The method for energizing an unenergized object for stimulating biological processes according to claim 9 wherein the unenergized object consists of at least one material selected from the material group consisting of paper, plastics, polyesters, synthetic textiles, cellulose, materials at least partially made from cellulose, cotton, cotton containing materials, silk, linen, ramie, rayon, leather, materials at least partially made from collagen, sugars, and other materials containing noncentrosymmetric molecules.

11. The method for energizing an unenergized object according to claim 10 wherein the energized object is placed in proximity to a biological process for stimulation.

12. A method for energizing an unenergized object for stimulating biological processes, comprising:

positioning at least one unenergized object in proximity to a means for energizing the unenergized object, the means for energizing the unenergized object comprising, a radiation source capable of emitting radiation having a wavelength between $10^{-3}$ nm and $10^3$ nm incident to a crystal disposed proximate to the unenergized object, whereby the unenergized object transforms into an energized object usable for stimulating biological processes.

13. The method for energizing an unenergized object for stimulating biological processes according to claim 12 wherein the unenergized object is comprised of a material including a non-crystalline anisotropic texture.

14. The method for energizing an unenergized object for stimulating biological processes according to claim 13 wherein the non-crystalline anisotropic texture at least partially consists of noncentrosymmetric molecules.

15. The method for energizing an unenergized object for stimulating biological processes according to claim 12 wherein the energizing means is comprised of:

at least one radiation source capable of emitting radiation having a radiation wavelength between $10^{-3}$ nm and $10^3$ nm; and the radiation being incident to and contiguous to at last one ungrounded crystal having at least one external line angle.

16. The method for energizing an unenergized object for stimulating biological processes according to claim 15 wherein the ungrounded crystal attaches to an electrically nonconducting material.

17. The method for energizing an unenergized object for stimulating biological processes according to claim 15 wherein the ungrounded crystal comprises at least one element selected from the element group consisting of aluminum, antimiony, arsenic, barium, beryllium, boron, bromine, cadmium, calcium, carbon, cesium, chlorine, chromium, cobalt, copper, fluorine, gold, hydrogen, iodine, iron, lithium, lead, magnesium, manganese, mercury, molybdenum, nickel, nitrogen, oxygen, palladium, phosphorus, platinum, potassium, radium, selenium, silicon, silver, sodium, strontium, sulfur, tellurium, tin, titanium, tungsten, uranium, vanadium, zinc, and zircon.

18. The method for energizing an unenergized object for stimulating biological processes according to claim 15 wherein the crystal consists of at least one ion selected from the ion group consisting of aluminum, antimony, arsenate, borate, cadmium, calcium, carbide, carbonate, cesium, chromate, chromium, cobalt, copper, halide, hydride, iron, lithium, magnesium, manganese, mercury, molybdate, nickel, nitrate, nitrite, oxide, palladium, phosphate, platinum, potassium, selenium, silicate, silver, sodium, sulfide, sulfite, tin, tungstate, vanadate, and zinc.

19. The method for energizing an unenergized object for stimulating biological processes according to claim 15 wherein the crystal is comprised of at least one mineral selected from the mineral group consisting of albite, amethyst, anhydrite, apatite, aragonite, azurite, barite, beryl, biotite, borax, brochantite, bromellite, calcite, carnotite, celestite, chalcocite, chromite, corundum, cristobalite, crocoite, cryolite, diamond, diaspore, diopside, dolomite, fluorite, garnet, halite, hornblende, ice, lazulite, leucite, malachite, mercury, microcline, muscovite, nepheline, niter, opal, orthoclase, periclase, pyrite, quartz(es), realgar, rutile, scheelite, silver, sodalite, sulfur, sylvite, tellurium, titanite, tourmaline, tremolite, turquoise, willemite, wolframite, wulfemite, and zircon.

20. An object for stimulating biological processes, comprising:

an inanimate object energized by placing the object in a crystal photon field, the crystal photon field generated by a radiation source capable of emitting radiation between $10^{-3}$ and $10^3$ nm, the radiation source being incident upon a crystal such that the crystal photon field is generated.

* * * * *